(12) United States Patent
Blomberg et al.

(10) Patent No.: US 7,689,275 B2
(45) Date of Patent: Mar. 30, 2010

(54) METHOD AND APPARATUS FOR DETERMINING AN EMG SIGNAL

(75) Inventors: Urban Blomberg, Solna (SE); Fredrik Jalde, Bromma (SE)

(73) Assignee: Maquet Critical Care AB, Solna (SE)

( * ) Notice: Subject to any disclaimer, the term of this patent is extended or adjusted under 35 U.S.C. 154(b) by 0 days.

(21) Appl. No.: 10/579,980

(22) PCT Filed: Nov. 18, 2004

(86) PCT No.: PCT/SE2004/001690

§ 371 (c)(1),
(2), (4) Date: Mar. 26, 2007

(87) PCT Pub. No.: WO2005/048839

PCT Pub. Date: Jun. 2, 2005

(65) Prior Publication Data

US 2007/0276280 A1    Nov. 29, 2007

(30) Foreign Application Priority Data

Nov. 19, 2003  (SE)  .................................. 0303061

(51) Int. Cl.
| | |
|---|---|
| A61B 5/04 | (2006.01) |
| H03F 1/26 | (2006.01) |
| H04B 15/00 | (2006.01) |
| G01R 23/02 | (2006.01) |
| H03D 3/00 | (2006.01) |
| H03K 13/00 | (2006.01) |
| A61M 15/00 | (2006.01) |
| F16K 1/08 | (2006.01) |

(52) U.S. Cl. ...................... 600/546; 600/509; 702/191; 327/39; 381/94.2; 128/203.14; 128/204.23

(58) Field of Classification Search ................ 600/546; 128/203.14, 204.23; 381/94.1–94.3; 327/39; 702/190–191

See application file for complete search history.

(56) References Cited

U.S. PATENT DOCUMENTS

| | | | |
|---|---|---|---|
| 5,524,632 A | * | 6/1996 | Stein et al. .................. 600/546 |
| 5,671,752 A | * | 9/1997 | Sinderby et al. ............ 600/546 |
| 5,768,392 A | * | 6/1998 | Graupe ....................... 381/94.3 |
| 5,800,470 A | | 9/1998 | Stein et al. |
| 6,411,843 B1 | | 6/2002 | Zarychta |
| 6,816,744 B2 | | 11/2004 | Garfield et al. |
| 2005/0011519 A1 | | 1/2005 | Sinderby |

* cited by examiner

*Primary Examiner*—Max Hindenburg
*Assistant Examiner*—John Pani
(74) *Attorney, Agent, or Firm*—Schiff Hardin LLP

(57) ABSTRACT

A method and apparatus for filtering an electromyogram (EMG) signal from a raw signal which includes a contribution from an electrocardiogram (EKG) signal is disclosed. The method includes the steps of estimating an attribute (such as a Fourier transform) of both the EMG contribution to the raw signal and the EKG contribution to the raw signal and, dependent on both frequency spectrums, determining an EMG window in a frequency range and obtaining the EMG signal by passing it through a filter defined by the frequency range. The method is particularly used when monitoring a multi-channel electrical recording from a plurality of electrodes attached to a patient's diaphragm.

14 Claims, 4 Drawing Sheets

METHOD AND APPARATUS FOR DETERMINING AN EMG SIGNAL

BACKGROUND OF THE INVENTION

1. Field of the Invention

The present invention concerns a method for determining an EMG-signal out of a raw signal obtained via a number of electrodes that interact with a patient to detect signals from the patient's diaphragm, the signals being supplied from the electrodes via respective signal channels.

2. Description of the Prior Art

Sensing of the EMG-activity in a patient's diaphragm by placing a catheter with a number of electrodes down the esophagus is a known technique, which is described in, among others, U.S. Pat. No. 5,671,752. The EMG-signals, which are receiving by handling the signals, can be used in connection with mechanical ventilation of patients, which is described, among others, U.S. Pat. No. 5,820,560 and PCT Application WO 98/48877.

Sensing of the EMG-activity from the diaphragm can even be done outside the body by placing electrodes on the patient, described, for example, in U.S. Pat. No. 4,248,240.

The physiological activity in the diaphragm generates a relatively weak electrical signal. This is so in particular if it is compared with the considerably stronger physiological (and electrical) activity in the heart (EKIG-activity). Therefore, the present desire is to attain in the best way the highest quality possible for the signal handling of the raw signal which the sensors detect, so that the resulting EMG-signal in the highest degree possible corresponds to the physiological activity. This is evident even in PCT Application WO 01/03579. In PCT Application WO 01/03579 it is assumed that the electrodes location in relation to the center of the diaphragm is known. Then the electrodes are measures based on location and symmetry, in which the EKG signal is measured in a traditional way.

Previously known methods for compensating for the EKG signal include, among others, using a band-pass filter which filters out the frequencies where the EKG signal normally appears. It is also known to measure the EKG signal separately and then remove an equivalent signal from the measured EMG signal.

A specific problem which is present with interference from EKG-activity is that the frequency spectrum for the physiological EKG-activity partially overlaps the frequency spectrum for the physiological EMG-activity. Moreover, there is the fact that the EKG-disturbances appear at different time points in relation to the breathing cycle.

None of the above-described methods consider the actual disturbance the EKG signal creates in a particular measuring situation in a particular patient. This disturbance also varies with time.

The known techniques also fail to consider that the respective frequency spectrum for EMG and EKG can vary between measurements in different people.

SUMMARY OF THE INVENTION

An object of the present invention is to provide a device and a method which lead to an improvement of known methods and procedures to filter out EMG-signals.

Another goal with the invention is to provide a device which can lead to an improved filtering of a raw signal to receive an EMG-signal.

The basis of the invention is that an EKG-signal and an EMG-signal are first estimated out of the raw signal. An appropriate detection window for determining the EMG-signal can then be determined from the estimated signals. In this connection, the detection window can be determined with reference to the sensitivity, width (frequency) or position in the frequency plane. The determination can even be made from a combination of two or more of these different possibilities.

In that way the invention makes possible an adaptable filtering of the EMG signal by measuring the actual frequency range for the respective EMG and EKG signal at each opportunity when the board frequency for the filter is to be determined.

An example of determining sensitivity is to first identify the frequency, where the EKG-interference becomes weaker than the EMG-signal. For that overlapping frequency region the EMG-signal is determined according to a first criterion (harder filtering, subtraction of estimated EKG-interference, etc). In the non-overlapping part, the EMG-signal is determined according to another criterion. In other words, the EMG-window is divided in two (or more) sub-windows, each with different signal handling conditions.

An example of variation of the width of the detection window is to first identify the frequency where the EKG-disturbance becomes weaker than the EMG-signal. The size of the detection window is then chosen to correspond to the distance from this frequency and the remaining part of the detected EMG-spectrum.

An example of variation of the position of the detection window is to first identify the frequency where the EKG-disturbance becomes weaker than the EMG-signal. Then the entire detection window is displaced so that this starting point coincides with the determined frequency.

In a further development of the method, consideration is taken to the noise level. IN this connection, the detection window can also be limited to fall within the region where the EMG-signal is stronger than the noise.

DESCRIPTION OF THE PREFERRED EMBODIMENTS

Figure 1:
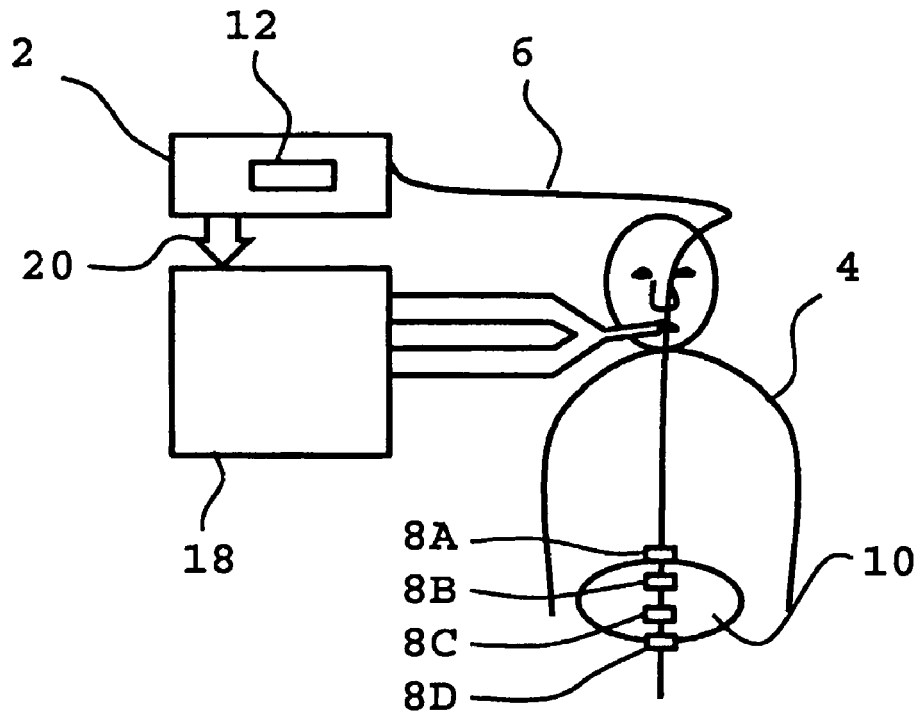
FIG. 1 shows a device according to the invention connected to a patient who is receiving respiratory therapy.

FIG. 1 shows a device 2 for determining EMG-signals according to the invention. The device 2 can in a known way be connected to a patient 4 via a catheter 6 with a number of electrodes 8A, 8B, 8C 8D in the tip (four electrodes are shown, but the number can be larger or smaller). By placing the catheter 6 in esophagus (gullet) of the patient 4, the electrodes 8A, 8B, 8C, 8D can be placed in different locations in the diaphragm 10 (whose size is exaggerated in the figure to indicate the relative placement of the electrodes 8A, 8B, 8C, 8D). In an analysis unit 12 in the device 2, filtering and analysis of the raw signal from the catheter 6 is done to extract the highest quality EMG-signal possible, i.e. an EMG-signal which corresponds to the physiological EMG-activity.

Figure 2:
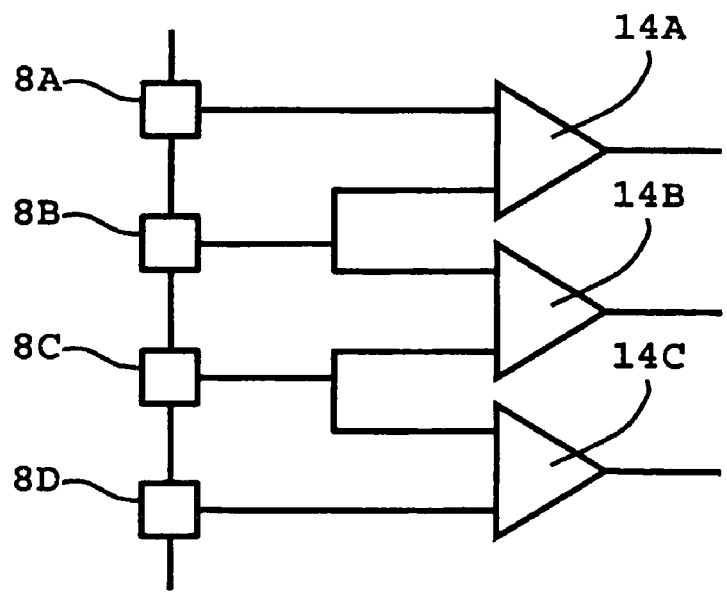
FIG. 2 shows a first example of an electrode connection to receive a raw signal.
Figure 3:
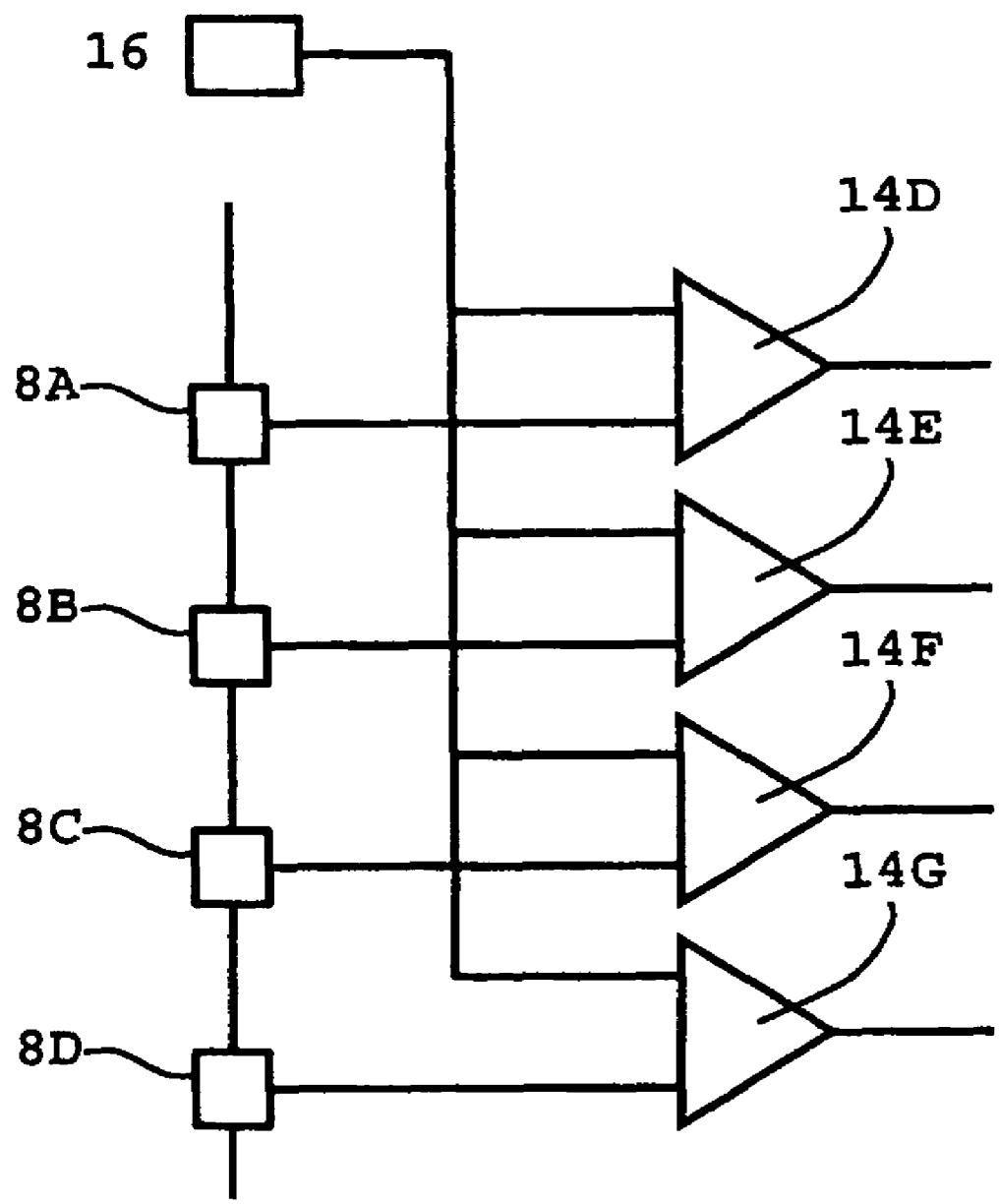
FIG. 3 shows a second example of an electrode connection to receive a raw signal.

In this connection, the raw signal can be received in many different ways. FIG. 2 and FIG. 3 exemplify two ways. In FIG. 2 it is evident that the electrodes 8A, 8B, 8C, 8D can be connected in pairs via three couplers 14A, 14B, 14C and thereby give rise to a three channel raw signal (with e.g. nine electrodes, eight channels are received in a corresponding way).

In FIG. 3 an example is shown where the respective electrodes 8A, 8B, 8C, 8D are connected to a reference electrode 16 (which e.g. can be grounded) via four couplers 14D, 14E, 14F, 14G. This gives rise to a four channel raw signal (for eight channels in this configuration, eight electrodes and a reference are consequently required).

More information regarding the catheter, the sensors and the entire process to capture raw signals from the diaphragm via the esophagus is given in e.g. U.S. Pat. No. 5,671,752 and PCT Application WO 01/03579. As noted, electrodes connected outside the body can be used instead for receiving EMG-signals completely non-evasively.

The patient 4 can even be connected in a conventional way to a ventilator system 18, which can be connected to a device 2. The respiratory therapy, which is given via the ventilator system 18, can in that way be influenced by the EMG-signal which is extracted from the raw signal from the diaphragm 10. This influence can be done in many different ways, of which some are described in U.S. Pat. No. 5,820,560 and PCT Application WO 99/43374.

The present invention is directed to a device 2 and, to be precise, the analysis unit 12. The analysis unit 12 filters EMG-signals out of the raw signal from the catheter 6. In this connection, a number of signal channels are used, as noted above.

To receive the highest quality EMG-signals possible, the filtering in the analysis unit 12 is done according to the method described below, which can be performed analog, digital or in a combination of these and realized in hardware, software of a combination of these.

Figure 4:
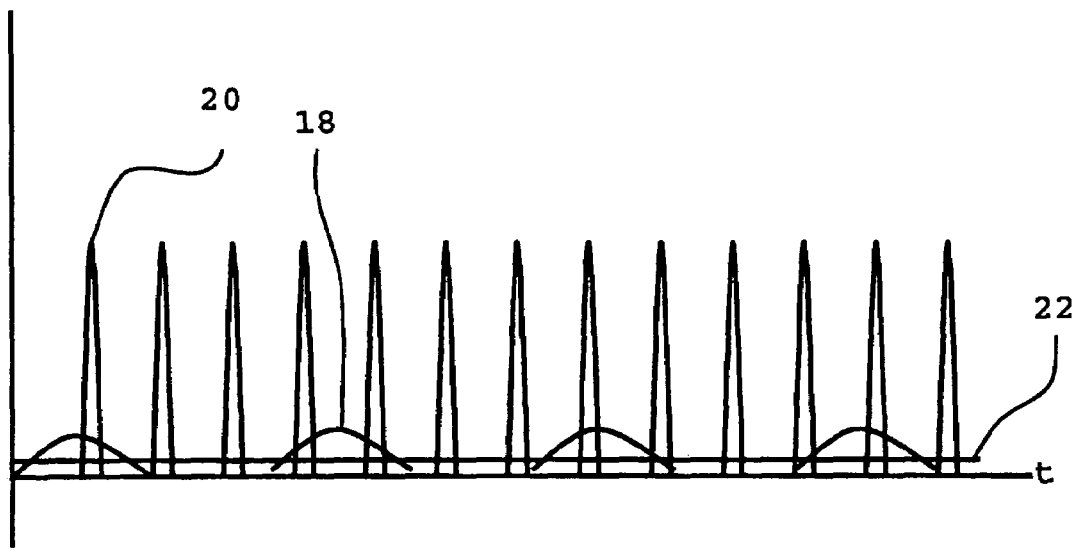
FIG. 4 shows schematically how the EKG-activity can affect detection of the EMG-activity over time.

One of the biggest interferences in measuring physiologic EMG-activity (determining of a representative EMG-signal) comes from the heart. FIG. 4 shows schematically how a number of EMG-activities 18 (representing the electrical activity of the diaphragm during inhalation) periodically are flooded by considerably stronger EKG-activities 20. Since breathing (the EMG-activity 18) as well as heart beat (the EKG-activity 20) have different periodicity (which in itself is variable), the signals do not coincide in a regular or predictable way, which makes the determination of the EMG-signal out of the raw signal more difficult.

FIG. 4 also shows a noise 22, which also contributes to making the measurement of EMG-activity 18 more difficult.

Figure 5:
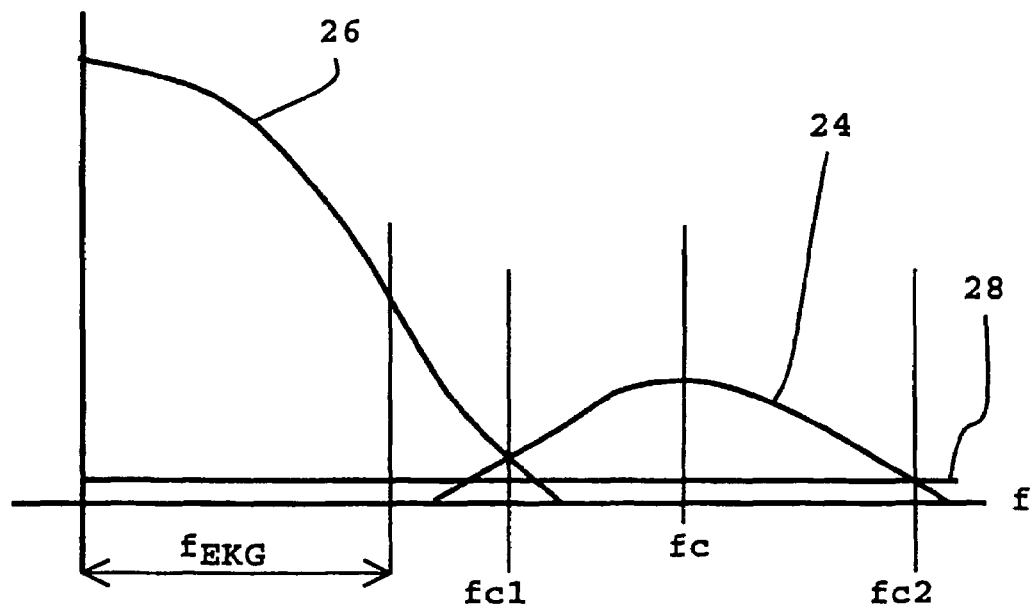
FIG. 5 shows schematically how frequency spectra for EKG and EMG partially overlap and how the method according to the invention can be designed.

FIG. 5 shows schematically how an EMG-signal 24 and an EKG-signal 26 partially contain overlapping frequency regions in their respective (physiological) frequency spectra. With a frequency analysis limited to the frequency region of the EMG-signal 24, it cannot therefore be excluded that the EKG-signal 26 gives a certain contribution. At the same time, a limiting of the frequency region which is analyzed should result in a larger uncertainty in the filtering of the EMG-signal 24 as the total EMG-energy risks being too small to effectively be detected.

FIG. 5 shows also a noise 28, which in this case comprises a white background noise with relatively constant energy content within the entire frequency region. Like the EKG-signal 26, the noise 28 results in the frequency region for detection of the EMG-signal 24 being limited.

With help from FIG. 4 and FIG. 5, different examples of the method according to the invention can be described. As is evident from FIG. 4, during each inhalation 18, one or a number of EKG-activities 20 regularly overlap. By analyzing the EKG-signal 26 within a frequency interval FEKG and at the same time estimating the frequency spectrum of the EMG-signal 24, the EKG-signal's 26 appearance within the overlapping part of the EMG-signal's 24 frequency spectrum can also be estimated. This in turn can be used to influence how the EMG-analysis is to advance.

A first way is then to determine a lower frequency border $fc1$, where the EKG-signal 26 and the EMG-signal 24 intersect, and let this frequency $fc1$ constitute the lower border in an analysis window for the EMG-signal (EMG-window). The upper border for the EMG-window can be determined in a corresponding way to an upper border frequency $fc2$, where the EMG-signal 24 intersects the noise signal 28. The lower border frequency $fc1$ is set in the same way in the absence of EKG signal.

According to this process, the EMG-window should be adjusted to its frequency width for, in principle, each detection. Yet this analysis involves at the same time that the noise energy contribution varies since the EMG-window width varies. Assuming that the noise is relatively constant within the frequency spectrum where the EMG-window width is going to vary, that varying contribution from the noise can be compensated for each determination.

It should be noted that it is not necessary to directly use the lower border frequency $fc1$ as a starting point for the EMG-window. The determination of the EKG-signal 26 also gives a determination regarding the slope for the EKG-signal 26 at the lower border frequency $fc1$. In this connection, if the EKG-signal 26 is flat, there can be reason to displace the EMG-window even more as the contribution from a flat EKG-curve decreases more slowly than the contribution from a steep EKG-curve. In other words, the EMG window is displaced nearer the EMG signal's middle frequency of so that the contribution from the EKG signal reduces to increase the safety margin.

Al alternative way to analyze the EMG-signal according to the invention is to instead use an EMG-window with constant width, but use a lower border frequency $fc1$ as a starting point for the EMG-window (which then can extend longer than to the upper border frequency $fc2$). In that way, a substantially constant contribution from the noise-signal 28 will be received.

In the same way as above, the slope (derivative) of the EKG-curve 26 at the lower border frequency $fc1$ can also be used to further finely adjust the placement of the EMG-window.

Yet another alternative way to analyze the EMG-signal 24 according to the invention is to use a constant EMG-window, which is big enough to contain the entire EMG-signal, but which falls outside the internal fEKG. From the estimate of the EKG-signal 26 which is made, the contribution which the EKG-signal entails for frequency (or total) can then be determined, which then is subtracted from the EMG-window. In principle, an "undisturbed" EMG-signal can be determined in this way (after subtraction of the contribution from the noise).

It is also possible to use the estimate of the EKG-signal 26 in such a way that the EMG-window is divided into sub-windows with different sensitivity or weighing.

That which is mentioned above can also be performed for the entire noise signal 28 (which can be estimated within a frequency region over the highest frequencies of the EMG-signal).

There are further ways to use the determination. In principle, the above has an immediate adaptation of the EMG-window occurred (in real time or with backlog) on the raw signal, i.e. a use of each specific EMG-activity (breath).

A slower adjustment of the EMG-window is possible, too, where trends over time are used to successively adjust the EMG-window. An advantage of slower adaptation is that patient-specific properties in the raw signal can be used in another way than with the immediate adjustment.

It can even be noted that the frequency spectra for the EMG-signal 24 as well as the EKG-signal 26 are not constant but can vary (within physiological borders).

In particular, the middle frequency for the frequency spectrum of the EMG-signal 24 can be displaced. This principally occurs dependent on changes within the patient, e.g. muscle fatigue or a reaction to the amount of relaxing medications which may have been given.

Minding the middle frequency can therefore be used in many different ways for the treatment. For example, an alarm can be generated at too high or fast variations in displacement of the middle frequency. Increased breathing support can be suggested to the operator or initiated automatically if the middle frequency is displaced beyond a border limit. The level of relaxing medication can be watched by studying the middle frequency variation (and even be used to maintain a certain level of calm, i.e. for regulating the dosage of the calming medicine).

Figure 6:
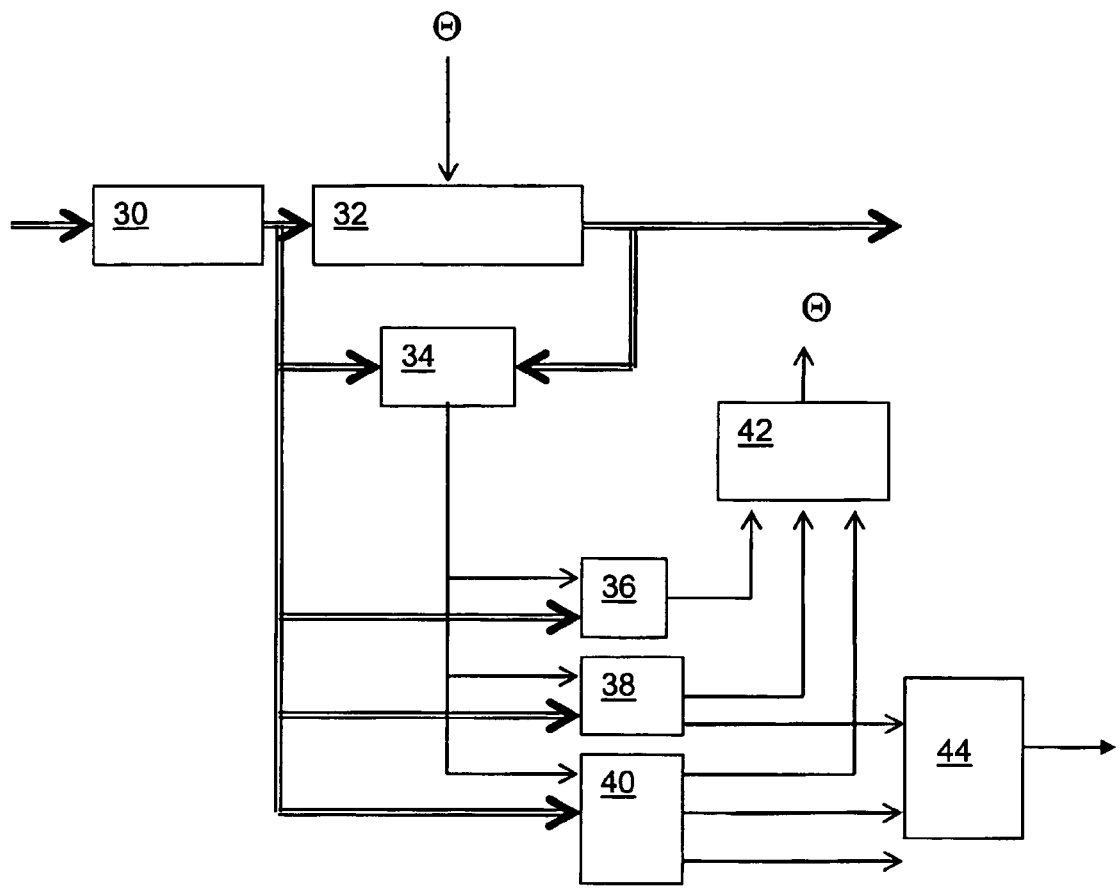
FIG. 6 shows a flow chart for an analysis unit according to the invention.

FIG. 6 shows a logical flow chart of an analysis unit 12 adapted to perform the method according to the above. The raw signal from the electrodes comes in via the catheter 6 to the analysis unit 12. After an AC-connection unit 30 the signal passes to an adaptive band-pass filter 32. The signal out from the band-pass filter 32 is a raw signal where the EKG signal is filtered out. This signal goes further to energy calculation which gives the desired EMG signal. The band-pass filter 32 uses a filter coefficient O, which is measured according to the description below. The signal from the AC-connection unit 30 and the output signal from the band-pass filter 32 are even fed to a time signaling block 34 whose output signal is a logical signal with four possible values: "not valid", "EMG", "EKG" and "noise". "not valid" means that no estimate of the signal will be made (if, for example, EKG is synchronous with EMG). If the value is EMG, EKG or "noise" it means that the respective spectrum can be estimated.

For estimating the different signals the output signal is fed from the AC-connection unit 30 to three different measuring units. A first 36 of these measuring units calculates the sum of noise and the EKG signal. A second measuring unit 38 calculates the sum of noise and the EMG signal. A third measuring unit 40 calculates noise only. The three measuring units are controlled by the logical output signal from the time signaling block 34. An output signal from the third measuring unit 40 is used for calculating energy. The output signal from the third is used to remove the energy level equivalent to the noise signal.

The output signal from the second measuring unit 38 and the third measuring unit 40 can even be used to calculate the middle frequency for EMG, which in that case is done in a calculating unit 44. For example, the middle frequency can be determined from the point of balance/mean for the filtered spectrum or alternatively maximum amplitude. As complimentary information the range of measurements/variance of the EMG signals spectra can be used. The variations of the middle frequency is a measure of muscle fatigue, and can also indicate that the patient is sedated, and in that case, how much. If the patient becomes exhausted an alarm can be sent, for example, or possibly ventilation assistance can increase.

The output signal from all the measuring blocks 36, 38 and 40 is fed to a filter optimizing block 42 which calculates the filter coefficient O for the band-pass filter 32.

Alternative methods exist to measure the spectrum in the blocks 36, 38 and 40. One alternative is to use Fourier analysis. Another alternative is to make an identification/adjustment of a model of the signal, for example, with the recursive method of least squares with forgetting factor, where the model's parameters are continually adapted to changes in the time signal.

Depending primarily on the cutting between the EMG spectra and the EKG spectra the filter order can be chosen. The filter should not be chosen unnecessarily sharp since this impacts the energy calculation in the time signal. Preferably, a steep filter with high ranking is chosen if the energy in the EKG signal decreases gradually in the region around the cut at the same time that the energy in the EMG signal increases gradually (that is, if the curves are flat). If the respective energy decreases or increases faster, a filter with lower ranking can be chosen.

In a later step the signal energy is determined. Since the bandwidth varies even the noise's energy contribution will vary. For a chosen pass band the energy is calculated for noise plus EMG. Therefore the energy spectrum of the noise is used to compensate so that a constant energy contribution is received which corresponds to a constant pass band.

Alternatively one could use a constant width in the pass band, since the critical region is that around the lower breaking frequency.

Those skilled in the art will understand that the flow chart shown in FIG. 6 is intended as a greatly simplified illustration of a working example and that an analysis unit to perform the method can be achieved in many different ways.

Preferably, the analysis unit comprises a computer program which directs the imputing units' function.

A number of algorithms and filter categories to sue for estimations and determinations according to the above are known to those skilled in the art and can be combined in many ways. There is therefore no need to describe them in more detail in this context.

Although modifications and changes may be suggested by those skilled in the art, it is the invention of the inventors to embody within the patent warranted heron all changes and modifications as reasonably and properly come within the scope of their contribution to the art.

The invention claimed is:

1. A method for determining an electromyogram (EMG) signal out of a raw signal comprising the steps of:
obtaining a plurality of signals from a subject via a plurality of electrodes configured to interact with the subject to detect signals from the diaphragm of the subject, each electrode having a signal channel associated therewith;
combining the respective signals of the signal channels to form a multi-channel raw signal that contains an electrocardiogram (EKG) contribution arising from an EKG signal of the subject and an EMG contribution arising from an EMG signal of the subject;
automatically electronically estimating an attribute of said contribution of said EKG signal of the subject to said raw signal and an attribute of said contribution of said EMG signal of the subject to said raw signal, to obtain an estimated EKG signal attribute and an estimated EMG signal attribute; and
dependent on the frequency spectrum of said estimated EKG signal attribute and the frequency spectrum of said estimated EMG signal attribute, automatically electronically determining an EMG window in a frequency range and frequency-domain filtering said raw signal only within said frequency range of said window to obtain said EMG signal as a filtered-out signal.

2. A method as claimed in claim 1 comprising filtering said EMG signal that is filtered out from said raw signal.

3. A method as claimed in claim 2 comprising automatically electronically dividing said window into at least two sub-windows with respectively different filtering criteria dependent on said estimated EKG signal attribute and said estimated EMG signal attribute.

4. A method as claimed in claim 1 comprising automatically electronically determining a width of said window dependent on said estimated EKG signal attribute and said estimated EMG signal attribute.

5. A method as claimed in claim 4 comprising automatically electronically determining a middle frequency of said estimated EMG signal and using said middle frequency as a measure of a degree of sedation of the patient.

6. A method as claimed in claim 5 comprising automatically using said middle frequency to regulate an amount of sedative administered to the patient.

7. A method as claimed in claim 1 wherein said window has a lower frequency, and automatically electronically determining said lower frequency of said window dependent on said estimated EKG signal and said estimated EMG signal attribute.

8. A method as claimed in claim 1 comprising determining said window as a window having a constant width starting from a lower frequency, and automatically electronically determining said lower frequency dependent on said estimated EKG signal attribute.

9. A method as claimed in claim 1 comprising automatically electronically estimating a noise signal attribute from said raw signal, and automatically electronically determining an upper frequency of said window dependent on said estimated EMG signal attribute and said estimated noise signal attribute.

10. A method as claimed in claim 1 comprising automatically electronically determining a middle frequency of said estimated EMG signal attribute, and using said middle frequency to monitor or measure at least one of muscle fatigue and muscle activity of the patient.

11. A method as claimed in claim 10 comprising automatically activating a humanly perceptible alarm dependent on deviation of said monitored or measured muscle fatigue from a reference value.

12. A method as claimed in claim 10 comprising automatically controlling a ventilator configured to interact with the patient to provide increased ventilation support to the patient dependent on said monitored or measured muscle fatigue.

13. A method as claimed in claim 1 comprising automatically electronically identifying a first derivative of a curve representing said estimated EKG signal attribute, and placing a lower frequency of said window dependent on said first derivative.

14. A method as claimed in claim 1 comprising using said estimated EKG signal attribute and said estimated EMG signal attribute to identify a frequency range within said raw signal wherein said contribution of said EKG signal is weaker than said contribution of said EMG signal, and comprising determining said frequency range of said EMG window to substantially coincide with said frequency range in which said contribution of said EKG signal is weaker than said contribution of said EMG signal.

* * * * *